United States Patent [19]
Gampp, Jr. et al.

[11] Patent Number: 5,893,877
[45] Date of Patent: Apr. 13, 1999

[54] SURGICAL INSTRUMENT WITH OFFSET HANDLE

[75] Inventors: Kurt W. Gampp, Jr., Wildwood; Gregg D. Scheller; Michael D. Auld, both of Chesterfield, all of Mo.; Robert F. Spetzler, Paradise Valley, Ariz.

[73] Assignee: Synergetics, Inc., St. Charles, Mo.

[21] Appl. No.: 08/920,349

[22] Filed: Jul. 16, 1997

Related U.S. Application Data

[63] Continuation of application No. 08/630,613, Apr. 10, 1996, abandoned.

[51] Int. Cl.$^6$ .................................................. A61B 17/32
[52] U.S. Cl. ................................................... 606/205
[58] Field of Search .............................. 606/205, 139, 606/142, 144, 167, 170, 171, 174, 175, 206–210

[56] References Cited

U.S. PATENT DOCUMENTS

| | | |
|---|---|---|
| 2,165,374 | 7/1939 | Heilig . |
| 2,898,915 | 8/1959 | Kammer . |
| 4,165,745 | 8/1979 | Heifetz . |
| 4,258,716 | 3/1981 | Sutherland . |
| 4,433,687 | 2/1984 | Burke et al. . |
| 4,598,711 | 7/1986 | Deniega . |
| 4,602,631 | 7/1986 | Funatsu . |
| 4,644,651 | 2/1987 | Jacobsen . |
| 4,760,848 | 8/1988 | Hasson . |
| 4,873,979 | 10/1989 | Hanna . |
| 4,938,214 | 7/1990 | Specht et al. . |
| 4,955,887 | 9/1990 | Zirm . |
| 4,995,876 | 2/1991 | Puig . |
| 4,997,436 | 3/1991 | Oberlander . |
| 5,122,150 | 6/1992 | Puig . |
| 5,141,514 | 8/1992 | van Amelsfort . |
| 5,184,625 | 2/1993 | Cottone, Jr. et al. . |
| 5,370,658 | 12/1994 | Scheller et al. . |

FOREIGN PATENT DOCUMENTS

| | | |
|---|---|---|
| 1026461 | 4/1953 | France . |
| 2091624 | 8/1982 | United Kingdom . |
| WO82/00968 | 4/1982 | WIPO . |

Primary Examiner—Gary Jackson
Assistant Examiner—Vikki Trinh
Attorney, Agent, or Firm—Howell & Haferkamp, LC.

[57] ABSTRACT

A surgical instrument comprises an instrument head and an instrument handle. The instrument head has a proximal end, a distal end, a head static part at the proximal end, a reciprocative part generally at the proximal end, and a moveable distal part at the distal end. The reciprocative part is operatively connected to the moveable distal part so that movement of the reciprocative part between forward and rearward positions causes movement of the moveable distal part between first and second positions. The instrument handle has a handle body attachable to the head static part of the instrument head, a handle plunger configured for reciprocating relative to the handle body generally along the instrument axis, and a lever arm. The handle plunger is operatively engageable with the reciprocative part of the instrument head when the head static part is attached to the handle body. Movement of the handle plunger between forward and rearward positions causes movement of the reciprocative part of the instrument head between its forward and rearward positions. The lever arm is connected to the handle body is engaged and laterally reciprocated by a hand of a surgeon. It is operatively connected to the handle plunger for moving the handle plunger between its forward and rearward positions as the lever arm is moved between inward and outward positions. The instrument handle is configured so that the lateral movement of the lever arm is in a plane spaced below the handle plunger to provide a forward line of sight generally along the instrument axis to the distal end of the instrument head as viewed from behind the handle plunger for permitting the surgeon's hand to reciprocate the lever arm without blocking the line of sight.

20 Claims, 3 Drawing Sheets

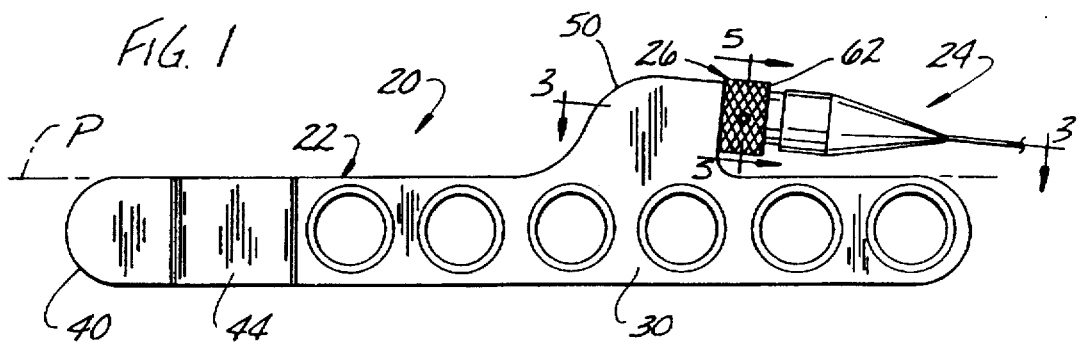
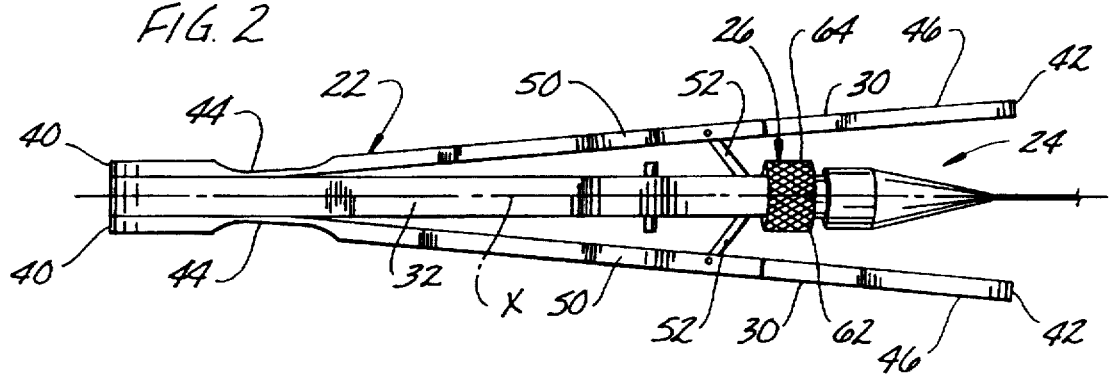
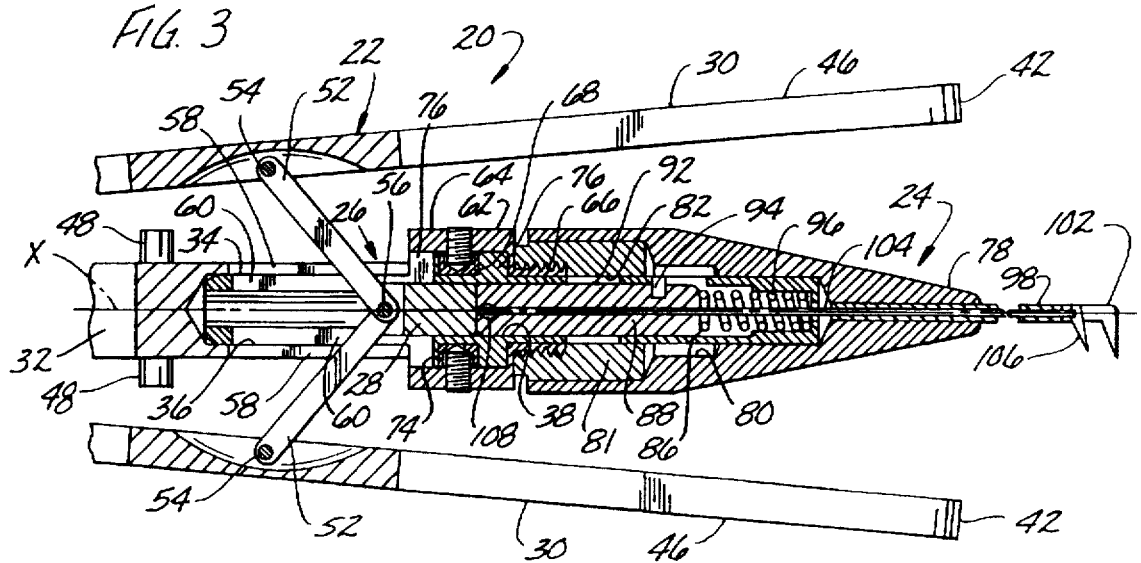

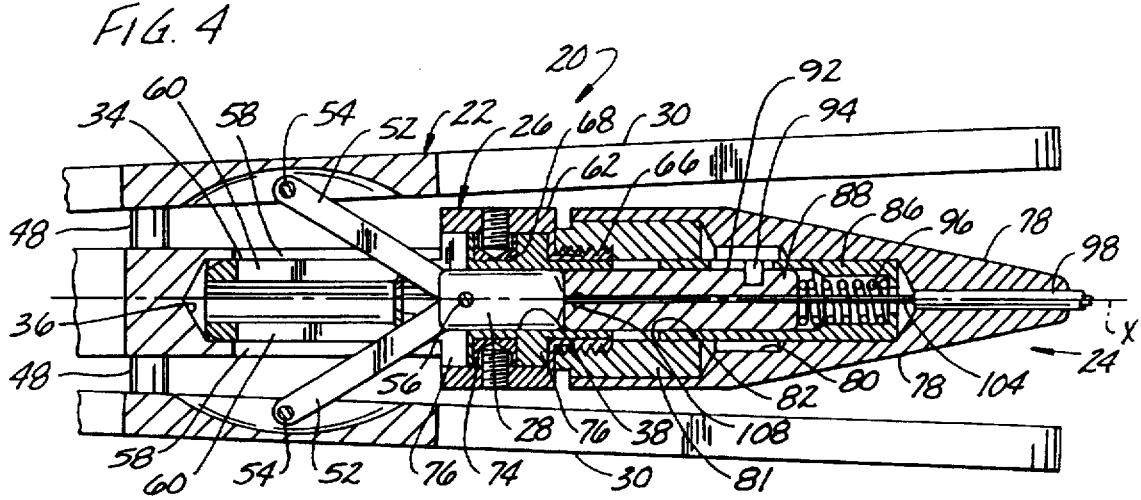
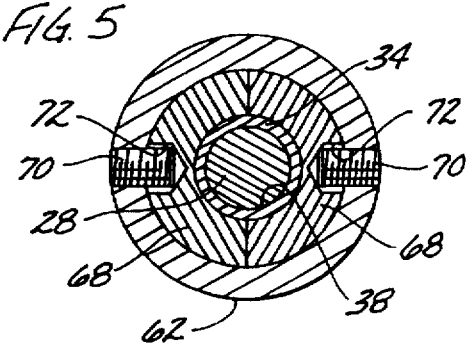
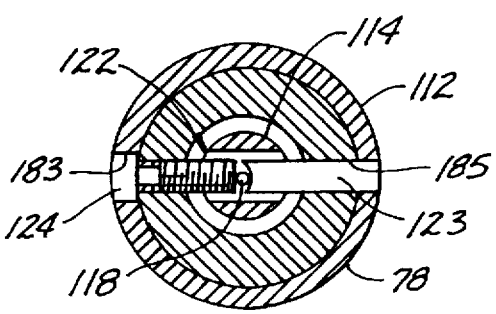
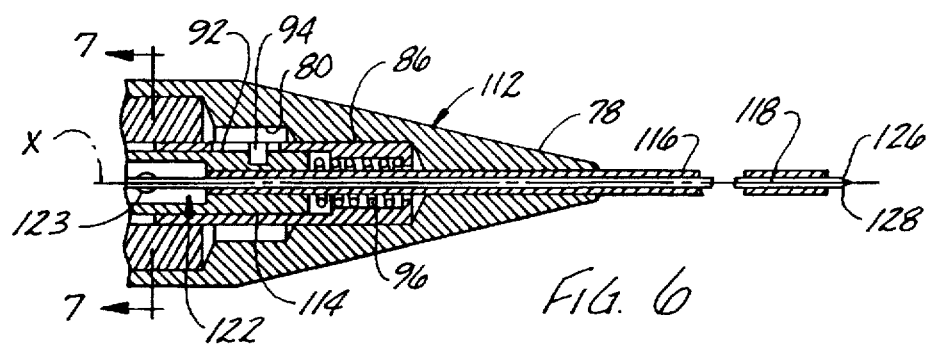
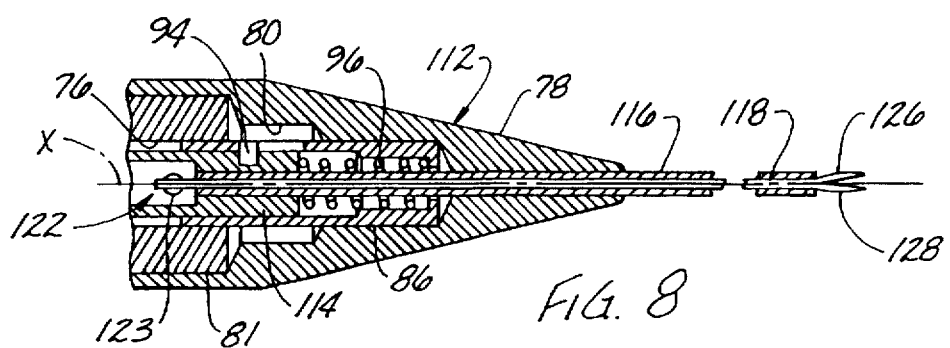

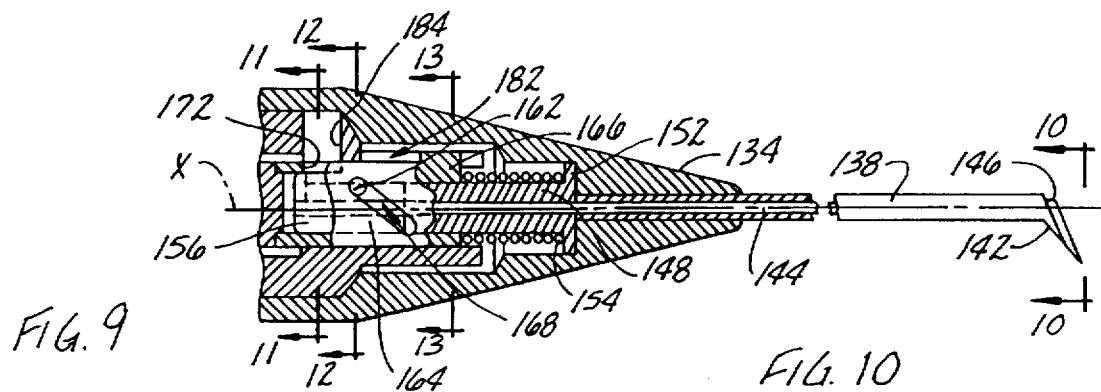
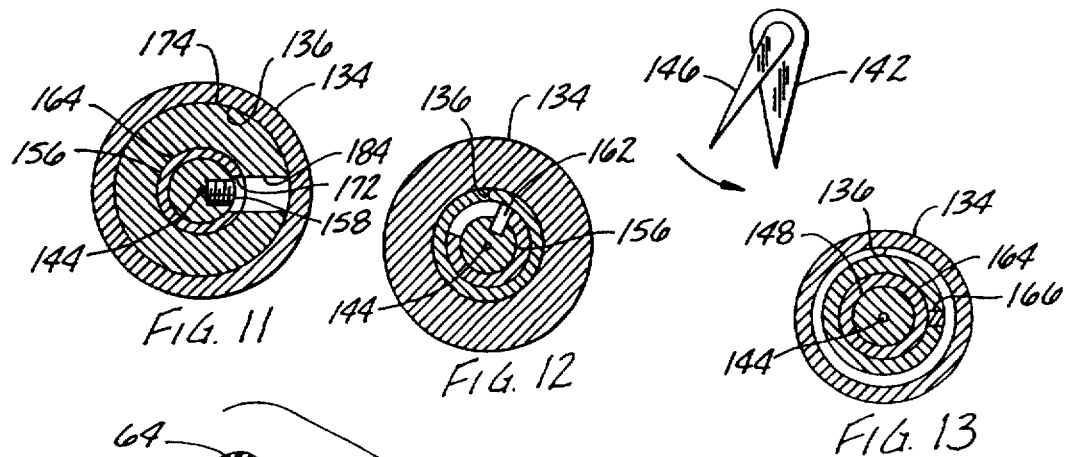
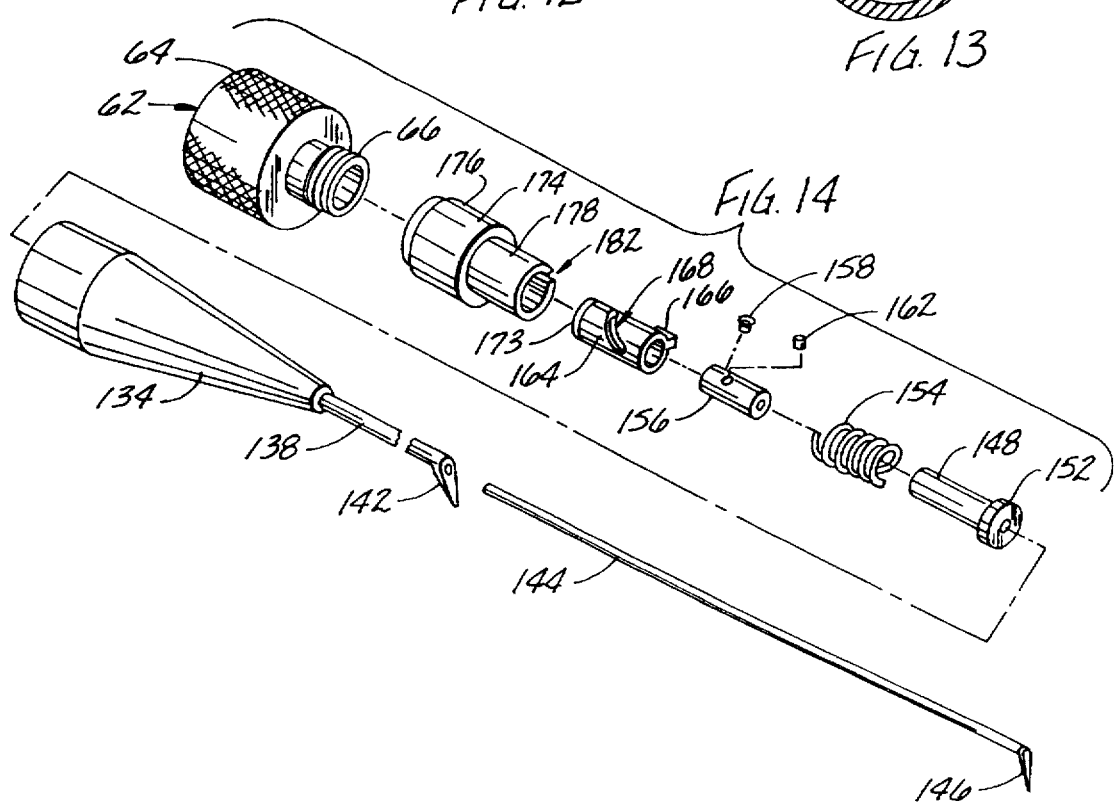

SURGICAL INSTRUMENT WITH OFFSET HANDLE

BACKGROUND OF THE INVENTION

This application is a continuation of prior U.S. application Ser. No. 08/630,613 filed Apr. 10, 1996 now abandoned.

This invention relates generally to microsurgical instruments.

In neurosurgery, or brain surgery, a surgeon performs a craniotomy (i.e., makes a small opening through the skull of a patient). Preferably, it is desirable for the opening to be small because the patient will recover much quicker than when neurosurgery is performed with a large portion of the skull removed. Therefore, when possible, neurosurgery will be performed through a craniotomy opening of about 20 mm in diameter.

When performing neurosurgery to remove a tumor or treat an aneurysm, once the craniotomy opening through the skull is made, the surgical site within the brain is accessed by progressively cutting deeper incisions through the infolds or fissures separating the convolutions of the brain. The incision through the fissures is made deep enough to access the surgical site. This positions the surgical site at a bottom apex of a generally cone-shaped incision that extends downwardly through the fissures of the brain. This cone-shaped incision is accessed through the circular opening of the craniotomy. With a typical craniotomy diameter of 20 mm, and considering the cone-shaped configuration of the incision that extends to the surgical site at the apex of the cone, access to the surgical site is very limited and difficult to view by the surgeon performing the surgery.

The difficulty of viewing the surgical site at the bottom apex of the incision cone is made even more difficult when one or more surgical instruments are used by the surgeon. Conventional neurosurgical instruments are usually constructed with elongate, slender configurations so as to not occupy much of the area providing access to the surgical site. However, when a surgeon is using such conventional neurosurgical instruments through the craniotomy opening and the incision through the brain fissures, the surgeons hands gripping the instrument are usually directly in a line of sight to the apex of the incision, thus interfering with the surgeon's view of the surgery. Furthermore, in neurosurgical instruments that have relative moving parts such as forceps, clamps and scissors, the handles of these instruments are operated by the surgeon's hands in much the same manner as tweezers are operated. To enable the relative lateral movements of the manually manipulated members of these handles, the handles must be laterally widened. This increase in the lateral width of these instruments also tends to obstruct the surgeon's view through the craniotomy opening when using such instruments.

SUMMARY OF THE INVENTION

Among the several objects of the present invention may be noted the provision of an improved neurosurgical instrument; the provision of such an instrument which avoids the disadvantages of conventional neurosurgical instruments; the provision of such an instrument with relative moving parts operated by manually manipulated handle levers; the provision of such an instrument in which the handle levers and the surgeon's hand gripping the handle levers are not in the line of sight of the surgeon when the operative portion of the instrument is inserted through a craniotomy opening during a surgical procedure; and the provision of such an instrument which is of relatively simple construction.

In general, a surgical instrument of the present invention comprises a surgical instrument head and a surgical instrument handle. The surgical instrument head has a proximal end, a distal end forward of the proximal end and insertable into a patient, a head static part (e.g., a head housing) at the proximal end, a reciprocative part (e.g., a head piston) generally at the proximal end, and a moveable distal part (e.g., a part of scissors, forceps, etc.) at the distal end. The moveable distal part is moveable relative to the head static part between a first position and a second position for enabling a surgeon to perform a surgical procedure on the patient. The reciprocative part is reciprocally moveable relative to the head static part generally along an instrument axis X between a forward position and a rearward position. The reciprocative part is operatively connected to the moveable distal part so that movement of the reciprocative part between its forward and rearward positions causes movement of the moveable distal part between its first and second positions. The surgical instrument handle has a handle body attachable to the head static part of the surgical instrument head, a handle plunger configured for reciprocating motion relative to the handle body generally along the instrument axis X between forward and rearward positions, and at least one lever arm. The handle plunger is operatively engageable with the reciprocative part of the surgical instrument head when the head static part is attached to the handle body. The handle plunger is configured so that movement of the handle plunger between its forward and rearward positions causes movement of the reciprocative part of the surgical instrument head between its forward and rearward positions. The lever arm is connected to the handle body for lateral movement thereof relative to the handle axis between inward and outward positions. The lever arm is configured for being engaged and laterally reciprocated between its inward and outward positions by a hand of a surgeon. It is operatively connected to the handle plunger for moving the handle plunger between its forward and rearward positions as the lever arm is moved between its inward and outward positions. The surgical instrument handle is configured so that the lateral movement of the lever arm is in a plane spaced below the handle plunger to provide a forward line of sight generally along the instrument axis X to the distal end of the surgical instrument head as viewed from behind the handle plunger for permitting the surgeon's hand to move the lever arm between its inward and outward positions without blocking the line of sight.

The surgical instrument head is releasably attached to the surgical instrument handle. It may perform any one of several different functions, such as surgical scissors, forceps, a surgical clamp which functions in the same manner as a forceps but provides a stronger gripping force, or a needle holder which is similar to a clamp but specifically designed to hold needles.

The surgical instrument handle is preferably provided with extended handles that project forwardly beyond the connection between the handle and the instrument head. These extended handle levers provide more leverage to the surgeon's hand for operating the instrument head and also position the surgeon's hand closer to the operative tip of the instrument head. This gives the surgeon a better feel and better control over movements of the instrument head tip.

Preferably, the instrument head is attached to the instrument handle in such a way that the instrument head may be freely rotated about the instrument axis without the need to rotate the levers of the instrument handle. This enables the repositioning of the operative tip of the instrument head relative to the surgical site without requiring the surgeon to move his/her hand to an awkward position.

Other objects and features will be in part apparent and in part pointed out hereinafter.

BRIEF DESCRIPTION OF THE DRAWINGS

FIG. 1 is a side elevational view of a neurosurgical instrument of the present invention having a surgical instrument head and a surgical instrument handle, the surgical instrument head being fragmented with a distal end thereof not shown;

FIG. 2 is a top plan view of the neurosurgical instrument of FIG. 1;

FIG. 3 is a cross-sectional view taken along the plane of line 3—3 of FIG. 1 showing levers of the surgical instrument handle in an outward lateral position;

FIG. 4 is a cross-sectional view similar to that of FIG. 3 but showing the levers in an inward lateral position;

FIG. 5 is a cross-sectional view taken along the plane of line 5—5 of FIG. 1;

FIG. 6 is a fragmented section view of a second embodiment of an instrument head of the present invention with forceps shown in a retracted position;

FIG. 7 is a cross-sectional view taken along the plane of line 7—7 of FIG. 6;

FIG. 8 is a fragmented section view similar to that of FIG. 6 but showing the forceps in an extended position;

FIG. 9 is a fragmented section view of a third embodiment of an instrument head of the present invention having scissors at its distal end;

FIG. 10 is an end view showing the scissors of FIG. 9;

FIG. 11 is a cross-sectional view taken along the plane of line 11—11 of FIG. 9;

FIG. 12 is a cross-sectional view taken along the plane of line 12—12 of FIG. 9;

FIG. 13 is a cross-sectional view taken along the plane of line 13—13 of FIG. 9; and FIG. 14 is an exploded perspective view of the instrument head of FIG. 9.

Corresponding reference characters indicate corresponding parts throughout the several views of the drawings.

DESCRIPTION OF THE PREFERRED EMBODIMENTS

Referring now to the drawings and more particularly to FIGS. 1–4, a neurosurgical instrument of the present invention is indicated in its entirety by the reference numeral 20. The neurosurgical instrument 20 comprises a surgical instrument handle, generally indicated at 22, and a surgical instrument head, generally indicated at 24, releasably attached to the surgical instrument handle. In the preferred embodiments of the invention all of the component parts of the instrument handle 22 and instrument head 24 to be described are constructed of materials that are capable of being sterilized, preferably alloys of titanium or aluminum to reduce the instrument's weight. However, it should be understood that the preferences set forth herein are not intended to be limiting and the instrument of the invention may be constructed from a variety of materials suitable for the purposes herein described.

The surgical instrument handle 22 comprises a handle body, generally indicated at 26, a handle plunger 28, and two lever arms 30. The handle body 26 includes a central main member (i.e., backbone 32) and a plunger housing 34 press fit into a longitudinal bore 36 in the backbone 32. The plunger housing 34 includes a longitudinal bore 38 sized and shaped for receiving the handle plunger 28. The handle plunger 28 is configured for reciprocating sliding motion in the bore 38 of the plunger housing 34 along an instrument axis X between a rearward position (FIG. 3) and a forward position (FIG. 4).

The lever arms 30 are elongate members having rearward ends 40 (left ends as viewed in FIGS. 1 and 2) and forward ends 42 (right ends as viewed in FIGS. 1 and 2). The lever arms 30 are fixed at their rearward ends 40 to opposite faces of the backbone 32. Preferably, intermediate regions 44 of the lever arms 30 adjacent the rearward ends 40 are of reduced thickness to permit forward portions 46 of the lever arms 30 (i.e., portions between the intermediate regions and the forward ends) to resiliently bend laterally at the intermediate regions between outward positions (FIG. 3) and inward positions (FIG. 4). Also preferably, the intermediate regions 44 of the lever arms 30 are configured to act as springs to bias the forward portions 46 of the lever arms in their outward positions. The lateral movement of the lever arms 30 is generally in a plane P which is generally perpendicular to the page of FIG. 1. Laterally extending pins 48 extend from the backbone 32 and engage the lever arms 30 when the lever arms are in their inward positions. These pins 48 act as stops to limit inward movement of the lever arms 30. Protrusions 50 extend upwardly from and move with the lever arms 30. Preferably, the protrusion 50 are integral with the lever arms 30 and are connected to the handle plunger 28 via links 52. Each link 52 has a first end pin-connected at 54 to one of the protrusion 50 and a second end pin-connected at 56 to the handle plunger 28. The links 52 extend through aligned longitudinal slots 58, 60 in the backbone 32 and plunger housing 34, respectively. Because of the links 52, movement of the lever arms 30 between their outward and inward positions causes movement of the handle plunger 28 between a rearward position (FIG. 3) and a forward position (FIG. 4). Preferably, the handle plunger 28 is in its rearward position when the lever arms 30 are in their outward positions and is in its forward position when the lever arms 30 are in their inward positions. The protrusion 50 and links 52 hold the handle plunger 28 above the plane P.

The handle body 26 further comprises a handle rotor 62 rotatably connected to the plunger housing 34 for rotation about the instrument axis X. The handle rotor 62 has a knurled nut 64, a threaded nipple 66 protruding forward of the knurled nut 64, and two semi-circular arcuate members 68. The threaded nipple 66 is sized and shaped for releasably receiving the instrument head 24. Two radially extending set screws 70 are threaded through the knurled nut 64 and extend into radial bores 72 in the semi-circular arcuate members 68. The set screws 70 compress the arcuate members 68 against each other to secure the arcuate members to the knurled nut 64. The two arcuate members 68 are sized and configured for riding in an annular channel 74 formed between two annular flanges 76 of the plunger housing 34. The annular flanges 76 and arcuate members 68 prevent longitudinal movement of the handle rotor 62 relative to the plunger housing 34 while facilitating free rotation of the rotor 62 relative to the plunger housing.

The various surgical instrument heads of the present invention are similar to the surgical instrument heads described in U.S. Pat. No. 5,370,658, incorporated herein by reference. The surgical instrument head 24 of this embodiment is constructed to perform a scissors cutting microsurgical operation where the cutting blades of the scissors are arranged to cut through a plane oriented at an angle relative to the instrument axis X (i.e., the longitudinal axis of the instrument handle 22). The instrument head 24 is comprised of a head housing 78 containing the component parts of the instrument. The exterior of the head housing 78 is generally cone shaped with the head housing tapering to a rounded point at its forward end (i.e., right hand end as viewed in the drawing figures), and the base of the housing at its rearward end (i.e., rearward end) having a cylindrical exterior surface with an exterior diameter substantially equal to the exterior diameter of the knurled nut 64 of the instrument handle 22. A stepped bore 80 comprised of four internal cylindrical sections each having a different internal diameter is formed through the center of the head housing 78. A first cylindrical insert 81 is press fit into the left end of the housing internal bore 80 and is held securely in a tight friction engagement in the internal bore. The first insert 81 has a hollow internal bore 82 extending through its center with a left hand portion of the bore having an internal screw thread formed therein. The internal screw thread of the bore 82 is determined to thread over the threaded nipple 66 of the handle rotor 62 and thereby releasably secure the instrument head 24 to the instrument handle 22 while permitting rotation of the instrument head relative to the plunger housing 34 (i.e., a stationary part of the handle). The first insert 81 and the head housing 78 constitute static (or non-reciprocating) parts generally at the proximal end of the instrument head 24. Although referred to herein as static parts, this is not meant to imply that the first insert 81 and head housing 78 do not move relative to stationary parts (e.g., the plunger housing) of the instrument handle 22. As discussed above, the entire instrument head 24 rotates with the handle rotor 62. A second tubular insert 86 is received in the head housing internal bore 80 and is slip fit and securely held in friction engagement in the third cylindrical section of the housing internal bore. The second insert 86 has a cylindrical interior bore and a head piston 88 is received within the bore of the second insert 86 for longitudinally reciprocating sliding movement therein. The head piston 88 constitutes a reciprocative part of the instrument head 24. A longitudinal slot 92 is formed through the side of the second insert 86 and a limit pin 94 secured in a side of the head piston 88 engages in the slot 92 and limits the longitudinal reciprocating movement of the head piston in the second insert. A coil spring 96 is positioned between the right hand end face of the head piston 88 as viewed in the drawing figures and the right hand end wall of the second insert 86. The spring 96 biases the head piston 88 to the left as viewed in the drawing figures.

A narrow hollow tube 98 is press fit and securely held in the fourth cylindrical section of the head housing internal bore 80 and projects out from the tip of the instrument head 24. The press fit engagement of the tube 98 in the head housing 78 securely holds the tube in friction engagement with the housing. The external diameter of the tube 98 is preferably about 0.89 mm to enable the tube to be inserted into very small incisions for preforming microsurgical operations with the surgical implements formed at the distal end of the tube yet to be described. At the distal end of the instrument head 24 (i.e., the right end of the tube 98 as viewed in the drawing figures) on one half of the tube wall is secured one scissors blade 102 (i.e., a non-reciprocating blade), the blade being positioned to perform a scissors cutting microsurgical operation across a plane arranged at an angle relative to the instrument axis X. In the preferred embodiment the one blade 102 is secured to the half of the tube end by a brazed, butt-joint connection. The friction engagement of the tube 98 in the head housing internal bore 80 holds the scissors blade 102 stationary relative to the head housing 78 and the instrument handle 22.

A narrow, cylindrical rod 104 is received for reciprocating, longitudinal linear movement inside the internal bore of the narrow tube 98. The distal end of the rod 104 (right end as viewed in the drawing figures) is formed in the configuration of a second scissors blade 106. The second scissors blade 106 constitutes a moveable distal part of the instrument head 24 connected to the reciprocative part (i.e., the head plunger 88) via the rod 104. When the rod 104 is caused to move in a longitudinally linear movement relative to the narrow tube 98 the scissors blade 106 formed on the end of the rod slides adjacent the scissors blade 102 formed on the end of the tube and together they perform a scissors cutting microsurgical operation across a plane oriented at an angle relative to the longitudinal axis of the instrument handle 22. The rearward end of the rod 104 projects from the tube 98 into the interior of the head housing 78 and extends through the end wall of the second insert 86, the coil spring 96, and through an internal bore extending longitudinally through the center of the head piston 88. The rearward end of the rod 104 is preferably secured to the head piston 88 via suitable set screws (not shown) and is moveable therewith. Movement of the head piston 88 between a rearward position (FIG. 3) and a forward position (FIG. 4) causes the rod 104 and second scissors blade 106 to move between rearward and forward positions. When the second blade 106 is in its rearward position (FIG. 3), it is rearwardly spaced from the first blade 102. When the second blade 106 is in its forward position, it overlaps with the first blade 102 to provide the cutting operation.

When the instrument head 24 is threadably secured to the threaded nipple 66 of the handle rotor 62, the head piston 88 engages the handle plunger 28. Movement of the handle plunger 28 between its forward and rearward positions causes movement of the head piston 88 between its forward and rearward positions. As discussed above, the handle plunger 28 is moved between its forward and rearward positions by the lever arms 30, and the second scissors blade 106 is moved between its forward positions by the head piston 88. Thus, moving the lever arms 30 between their outward and inward positions causes movement of the second scissors blade 106 between its rearward and forward positions.

To operate the neurosurgical instrument 20, a surgeon (not shown) grasps the lever arms 30 and operates the lever arms in a motion similar to operation of a pair of tweezers. In other words, the outer surfaces of the forward portions 46 of the lever arms 30 are grasped by the surgeon's thumb and index finger and the rearward portions of the lever arms rest on the dorsal side of the surgeon's hand. With the instrument 20 so positioned, the surgeon may move the second scissors blade 106 from its rearward position to its forward position by squeezing the lever arms 30 toward each other. As the surgeon lessens his/her grip on the lever arms 30, the resiliency of the intermediate regions of the lever arms causes the lever arms to move outward. Because the spring 96 biases the head piston 88 in its rearward position, outward movement of the lever arms 30 causes rearward movement of the second scissors blade 106 to open the scissors.

Preferably, the lever arms 30 are shaped and configured so that the forward ends 42 thereof extend forwardly beyond the head housing 78. These extended lever arms provide more leverage to the surgeon's hand for operating the instrument head 24 and also position the surgeon's hand closer to the operative tip (i.e., distal end) of the instrument head. This gives the surgeon a better feel and better control over movements of the instrument head tip. Because the surgeon's hand during operation of the instrument 20 is spaced approximately ½" below the instrument axis X, the surgeon has a clear forward line of sight generally along the instrument axis X to the distal end of the instrument head 24 as viewed from behind the handle plunger 28. Thus, during the normal and intended use of the instrument 20, the surgeon's hand does not block the line of sight.

Also, because the handle rotor 62 rotates freely relative to the plunger housing 34, the surgeon may easily rotate the instrument head 24 (including the scissors) about the instrument axis X by rotating the knurled nut with his/her other hand. Thus, the instrument head 24 may be freely rotated about the instrument axis without the need to rotate the lever arms of the instrument handle. This enables the repositioning of the operative tip of the instrument head 24 relative to the surgical site without requiring the surgeon to move his/her hand to an awkward position.

In a variation of the first instrument head 24 described above, the scissors blades 102, 106 may be replaced with a pair of opposed clamping jaws of a forceps where the jaw surfaces engage across a plane oriented at an angle relative to the longitudinal axis of the instrument handle 22. The operation of the forceps jaws is substantially identical to that of the scissors blades described above.

A second embodiment of an instrument head of the present embodiment is generally indicated at 112 in FIGS. 6–8. This embodiment has a microsurgical forceps formed as its surgical implement at the distal ends of the tube and rod. Many of the component parts of the instrument head 112 shown in FIGS. 7–9 are identical to component parts of the first embodiment of the instrument head 24 and these same component parts have the same reference numerals employed in describing those parts with reference to the first embodiment of the instrument head. In comparison to the first embodiment of the instrument head, the second embodiment also includes a head housing 78, a stepped internal bore 80 extending through the interior of the head housing and having four cylindrical sections each with different internal diameters, a first insert 81 with an internal bore 82 extending through the first insert. The first insert 81 is held in the internal bore 80 of the head housing 78 of this second embodiment of the instrument head in substantially the same manner as the insert of the first embodiment of the instrument head. A second insert 86 is also slip fit in the internal bore 80 of the head housing 78 of the second embodiment. The second insert 86 has the same construction as that of the first embodiment of the instrument head. The second insert also contains a coiled spring 96 in an identical manner to that of the first instrument head embodiment. The second instrument head differs from the first instrument head in the construction of the head piston 114 and the construction of the narrow tube 116 and narrow rod 118 extending from the right hand end of the head housing 78.

As seen in drawing FIGS. 6–8, the head piston 114 of the second embodiment of the instrument head is the same as that of the first embodiment in that it has a cylindrical configuration and is received for longitudinally reciprocating movement in the interior of the second insert 86. The head piston 114 is also provided with a limit pin 94 that engages in the longitudinal slot 92 of the second insert 86 and limits the longitudinal reciprocating movement of the head piston 114 in the internal bore of the second insert. The coil spring 96 engages against the forward end face of the head piston 114 at one end and against the end wall of the second insert 86 at its opposite end to bias the head piston to the left as viewed in the drawing figures.

The head piston 114 of the second embodiment differs from the head piston of the first embodiment in that the rearward end of the hollow narrow tube 116 is secured by a press fit friction engagement in the internal bore of the head piston. With the tube 116 attached to the head piston 114 in this manner it reciprocates longitudinally along the center axis X of the instrument handle with reciprocation of the head piston along this axis. The second embodiment of the head piston 114 further differs from the head piston of the first embodiment in that a lateral slot 122 is formed through the rearward end of the head piston. The lateral slot 122 is positioned relative to the head piston so that it aligns with the pair of diametrically opposed bore holes through the head housing 82 and through the first insert 78.

The narrow rod 118 is received in the interior of the narrow tube 116 for reciprocating longitudinally linear movement therein. The rearward end of the rod 118 projects from the rearward end of the tube 116 into the lateral slot 122 of the head piston. A cylindrical pin 123 with a V-shaped notch at its distal end is inserted through aligned bore holes 183 and 185 of the head housing and first insert, respectively. The pin is held securely in friction engagement in the bore holes and the V-notch of the pin engages against one side of the rod 118 left end. A screw 124 is screw threaded through the opposite aligned bore holes 183, 185 of the head housing and first insert, respectively, and engages against the opposite lateral side of the rod left end from the pin 123, thereby securing the rod 118 stationary relative to the head housing 82. From this described construction, it can be seen that as the head piston 114 is reciprocated along the instrument axis X, the tube 116 reciprocates along the axis with the piston and both the piston and tube reciprocate longitudinally in the head housing relative to the stationary rod 118.

At the right hand end of the rod 118, the rod is longitudinally split forming a pair of forceps jaws in the rod end. The forceps jaws 126, 128 are resiliently bent outward so that when the tube 116 is moved to the left in response to head piston 114 movement to the left, the forceps jaws project from the end of the tube and open as seen in FIG. 8. When the tube is moved to the right in response to head piston movement to the right, the right tube end causes the forceps jaws to close.

With the handle lever arms 30 in their outward positions shown in FIG. 3, the handle plunger 28 is retracted rearwardly (i.e., to the left) in the bore 38 in the plunger housing 34 and the coil spring 96 of the instrument head 112 biases the head piston 114 to the left as viewed in FIG. 8. The rearward movement of the head piston 114 retracts the forward end of the narrow tube 116 from its engagement over the forward end of the rod 118 and uncovers the pair of forceps jaws 124, 126 formed in the forward (distal) end of the rod. This enables the resiliency of the forceps jaws to open the jaws as shown in FIG. 9. As the lever arms 30 of the instrument handle are compressed laterally toward the central axis of the handle 22, the handle plunger 28 is pushed forward through the bore 38 of the plunger housing and pushes the head piston 114 to the right against the bias of the coil spring 96. The forward movement of the head piston 114 pushes the hollow tube 116 forward over the stationary rod 118, causing the forward end of the tube 116 to pass over the open jaws formed at the forward end of the rod 118 causing the jaws to close as shown in FIG. 6 to grip an object between the jaws. In this manner, the second embodiment of the instrument head 112 is employed with the previously described instrument handle 22 to perform microsurgical forceps gripping operations employing the forceps implement formed at the right end of the rod 118.

In a variation of the second instrument head embodiment 112 described above, the forceps jaws 126, 128 may be replaced by a pair of opposed scissors blades where the scissors blades slide across each other and perform a scissors cutting operation across a plane oriented parallel relative to the longitudinal axis X of the instrument handle 22. The operation of the scissors blades is substantially identical to that of the forceps jaws described above.

FIGS. 9–14 show a third embodiment of the instrument head 132 of the present invention designed to be employed with the previously described instrument handle 22. This embodiment of the instrument head 132 is used in performing microsurgical scissors cutting operations where the scissors of the instrument cut across a plane positioned parallel to the longitudinal axis of the instrument handle.

The third embodiment of the instrument head 132 is comprised of a head housing 134 having an exterior configuration substantially identical to that of the first two embodiments of the instrument heads. The head housing also has an internal bore formed between the left and forward ends of the housing, the internal bore having four interconnected cylindrical sections, each of different internal diameter. A narrow hollow tube 138 is press fit into the housing head internal bore 136 from the forward end of the housing. The rearward end of the tube 138 is securely held in friction engagement inside the housing bore. The forward end of the tube 138 has one blade 142 of a surgical scissors formed thereon. As seen in the drawing figures, the scissors blade 142 formed at the distal end of the narrow tube 138 is positioned relative to the tube to perform a surgical scissors cutting operation across a plane substantially parallel to the center axis of the instrument handle 22 and the third embodiment of the instrument head 132.

A narrow rod 144 is inserted through a center bore hole of the tube 138 and the rearward end of the rod projects from the left end of the tube into the head housing internal bore 136. The rod is received in the tube bore for rotational movement relative thereto but is prevented from moving in a longitudinally linear direction relative to the tube as will be explained. The forward end of the rod 144 is formed in the configuration of a second scissors blade 146. With the rod inserted in the interior of the tube 138, the rod scissors blade 146 and the tube scissors blade 142 slide across each other in response to the rod 144 being rotated through an arc segment to perform a scissors cutting operation between the two blades. As seen in the drawing figures, the scissors cutting operation performed by the surgical implement formed at the forward ends of the rod and tube cut across a plane substantially parallel to the center longitudinal axis of the instrument handle 22 in the third embodiment of the instrument head 132.

A first insert 148 is inserted into the housing internal bore 136. The insert 148 has a generally cylindrical configuration with a bore hole extending through its center and with an annular flange 152 formed at its forward end as viewed in the drawing figures. The flange 152 is press fit into a cylindrical section of the housing internal bore 136 and is thereby securely held in the bore. The internal bore of the first insert 148 is coaxial with the internal bore of the tube 138 and with the center axis of the instrument handle 22. The internal bore is dimensioned to receive the forward end of the narrow rod 144 therethrough enabling the rod to rotate freely within the internal bore. A coil spring 154 is positioned over the cylindrical exterior of the insert 148 with the spring engaging against the annular flange 152 at one end.

A cylindrical block 156 is positioned adjacent the rearward end of the first insert 148. The block has a center bore that aligns coaxially with the center bore of the first insert 148 and the rearward end of the narrow rod 144 is received in the block center bore. A set screw 158 is received in a threaded bore extending through one side of the block 156 and is tightened down in the threaded bore to securely grip the forward end of the rod 144 in the center bore of the block. With the rod 144 securely held to the block 156 by the set screw 158, as the block is rotated in the head housing interior 136, the rod 144 rotates with the block. A guide pin 162 is inserted into and securely held by friction engagement in a second bore hole in the side of the block 156. The guide pin 162 is employed in rotating the block through an arc segment about its center longitudinal axis in a manner to be described.

A reciprocating piston sleeve 164 is positioned over the block 156 and a portion of the first insert 148. The forward end of the reciprocating sleeve 164 engages against the left end of the coil spring 154 positioned around the first insert 148. The exterior surface of the sleeve 164 is generally cylindrical except for a projecting guide flange 166 adjacent the forward end of the sleeve. The guide flange serves to allow the sleeve to reciprocate in a longitudinally linear movement while preventing rotation of the sleeve about its center axis as will be explained. An angled slot 168 is cut through the exterior of the sleeve to its interior bore and the guide pin 162 of the block 156 engages in the slot. An access hole 172 is provided through the reciprocating sleeve 164 adjacent its rearward end. The access hole 172 is provided to enable access to the set screw 158 of the block 156 to tighten or release the set screw with the block received in the internal bore of the sleeve. An end cap 172 is secured to the rearward end of the reciprocating piston sleeve 164 and engages against the forward end face of the handle plunger 28. The engagement between the handle plunger 28 and the piston sleeve end cap 172 causes the sleeve to reciprocate longitudinally along the center axis of the handle 22 and the instrument head 132 in response to reciprocating movement of the handle plunger 28 along this axis.

A second insert 174 is press fit into the rearward end of the head housing internal bore 136. The second insert is comprised of two generally cylindrical sections 176, 178 with the first section 176 having a larger exterior diameter than the second section 178. A longitudinal slot 182 is cut through the second section 178 of the insert. The slot 182 is provided to receive the guide flange 166 of the reciprocating sleeve 164. A bore hole 184 is provided through the first section 176 of the second insert. The bore hole 184 is positioned through the insert first section so that it aligns coaxially with the bore hole through the rearward end of the reciprocating sleeve 164, providing access to the set screw of the block 156.

From the assembly of the component parts of the third embodiment of the instrument head 132 described above and shown in FIGS. 9–14, it can be seen that with the instrument head releasably secured to the threaded neck 34 of the instrument handle 22, manipulation of the handle lever arms 30 laterally toward and away from the handle center axis imparts reciprocating movement to the handle plunger 28 which in turn imparts reciprocating movement to the instrument head reciprocating piston sleeve 164. As the reciprocating sleeve 164 is pushed by the handle plunger 28 to the right as viewed in the drawing figures, the sleeve is constrained against rotational movement by engagement of the guide flange 156 in the longitudinal slot 182 formed in the second section of the second insert. As the reciprocating sleeve 164 is pushed through the interior bore of the second insert, the coil spring 154 is compressed and the angled slot 168 of the sleeve moves relative to the guide pin 162 of the block 156. The movement of the angled slot 168 relative to the guide pin 162 causes the block to rotate through an arc segment relative to the sleeve. The engagement of the forward end face of the block 156 with the rearward end face of the first insert 148 prevents the block from any longitudinal movement so that the block may only rotate in the instrument head interior. As the block rotates through the arc segment, the rod 144 secured in the internal bore of the block also rotates through the arc segment. Rotation of the rod 144 relative to the tube 138 causes the scissors blade 146 formed at the forward end of the rod to slide over the scissors blade 142 formed at the forward end of the tube, thereby performing a scissors cutting operation depicted by the arrow in FIG. 10. When the handle lever arms 30 are released from their compressed positions and allowed to resiliently bias laterally outward away from the center axis of the handle, the handle plunger 28 is retracted to the left as viewed in the drawing figures and the coil spring 154 pushes the reciprocating sleeve 164 rearwardly. Again, the sleeve is constrained from rotational movement by engagement of the guide flange 166 in the longitudinal slot 182 of the second insert. The longitudinal, linear movement of the sleeve 164 relative to the block 156 causes the angled slot 168 of the sleeve to move relative to the guide pin 162 and rotate the block back through the same arc segment. The rotation of the block back through the arc segment also rotates the rod 144 through the same arc segment and moves the scissors blade 146 formed at the right end of the rod relative to the scissors blade 142 formed at the right end of the tube to open the blades of the scissors implement. In this manner, the surgical scissors implement formed by the blades 142, 146 at the right ends of the respective tube and rod perform a microsurgical scissors cutting operation across a plane substantially parallel to the center axis of the instrument handle 22 in the third embodiment of the instrument head 132.

Although the third embodiment of the instrument head 132 is described above as performing a scissors cutting operation by the microsurgical implement formed at the forward ends of the tube and rod, the forward ends of the tube and rod may be modified to form forceps jaws in place of the scissors blades disclosed. Operation of this embodiment of the instrument head would then result in the microsurgical operation of clamping the forceps jaws at the forward ends of the tube and rod to grip an object positioned in a plane substantially parallel to the center longitudinal axis of the instrument handle and instrument head.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense. The invention therefore shall be limited solely by the scope of the claims set forth below.

What is claimed is:

1. A surgical instrument handle for use with an elongate surgical instrument head, the surgical instrument head having a proximal end, a distal end forward of the proximal end and insertable into a patient, a head static part at the proximal end attachable to the surgical instrument, a reciprocative part generally at the proximal end, and a moveable distal part at the distal end, the moveable distal part being moveable relative to the head static part between a first position and a second position for enabling a surgeon to perform a surgical procedure on the patient, the reciprocative part being reciprocally moveable relative to the head static part generally along an instrument axis X between a forward position and a rearward position, said reciprocative part being operatively connected to said moveable distal part so that movement of the reciprocative part between its forward and rearward positions causes movement of the moveable distal part between its first and second positions, the surgical instrument handle comprising:

a handle body comprising a handle stationary part and a handle rotor rotatably connected to the handle stationary part for rotation about the instrument axis X, the handle rotor being configured for fixedly receiving the head static part of the surgical instrument head so that rotation of the handle rotor relative to the handle stationary part causes like rotation of the surgical instrument head when the head static part is attached to the handle rotor;

a handle plunger configured for reciprocating motion relative to the handle body generally along the instrument axis X between forward and rearward positions, the handle plunger being operatively engageable with the reciprocative part of the surgical instrument head when the head static part is attached to the handle body, the handle plunger being configured so that movement of the handle plunger between its forward and rearward positions causes movement of the reciprocative part of the surgical instrument head between its forward and rearward positions; and at least one lever arm connected to the handle body for lateral movement thereof relative to the handle axis between inward and outward positions, said at least one lever arm being configured for being engaged and laterally reciprocated between its inward and outward positions by a hand of a surgeon, said at least one lever arm being operatively connected to the handle plunger for moving the handle plunger between its forward and rearward positions as said at least one lever arm is moved between its inward and outward positions;

said surgical instrument handle being configured so that said lateral movement of said at least one lever arm is in a plane spaced below the handle plunger to provide a forward line of sight generally along the instrument axis X to the distal end of the surgical instrument head as viewed from behind the handle plunger for permitting the surgeon's hand to move said at least one lever arm between its inward and outward positions without blocking the line of sight.

2. A surgical instrument handle as set forth in claim 1 further comprising a handle bore in the handle stationary part for receiving the handle plunger, said handle bore and said handle plunger being configured so that movement of said at least one lever arm between its inward and outward positions causes the handle plunger to move in the handle bore between its forward and rearward positions.

3. A surgical instrument handle as set forth in claim 1 wherein the handle plunger is linearly moveable between its forward and rearward positions.

4. A surgical instrument handle as set forth in claim 1 wherein the lever arm has a forward portion projecting forwardly beyond the handle body.

5. A surgical instrument handle as set forth in claim 4 wherein the forward portion of the lever arm projects forwardly beyond the head static part of the surgical instrument head when the head static part is attached to the handle body.

6. A surgical instrument handle for use with an elongate surgical instrument head, the surgical instrument head having a proximal end, a distal end forward of the proximal end and insertable into a patient, a head static part at the proximal end attachable to the surgical instrument, a reciprocative part generally at the proximal end, and a moveable distal part at the distal end, the moveable distal part being moveable relative to the head static part between a first position and a second position for enabling a surgeon to perform a surgical procedure on the patient, the reciprocative part being reciprocally moveable relative to the head static part generally along an instrument axis X between a forward position and a rearward position, said reciprocative part being operatively connected to said moveable distal part so that movement of the reciprocative part between its forward and rearward positions causes movement of the moveable distal part between its first and second positions, the surgical instrument handle comprising:

a handle body attachable to the head static part of the surgical instrument head;

a handle plunger configured for reciprocating motion relative to the handle body generally along the instrument axis X between forward and rearward positions, the handle plunger being operatively engageable with the reciprocative part of the surgical instrument head when the head static part is attached to the handle body, the handle plunger being configured so that movement of the handle plunger between its forward and rearward positions causes movement of the reciprocative part of the surgical instrument head between its forward and rearward positions;

at least one lever arm connected to the handle body for lateral movement thereof relative to the handle axis between inward and outward positions, said at least one lever arm being configured for being engaged and laterally reciprocated between its inward and outward positions by a hand of a surgeon, said at least one lever arm being operatively connected to the handle plunger for moving the handle plunger between its forward and rearward positions as said at least one lever arm is moved between its inward and outward positions; and at least one protrusion;

said surgical instrument handle being configured so that said lateral movement of said at least one lever arm is in a first plane spaced below the handle plunger to provide a forward line of sight generally along the instrument axis X to the distal end of the surgical instrument head as viewed from behind the handle plunger for permitting the surgeon's hand to move said at least one lever arm between its inward and outward positions without blocking the line of sight, the instrument axis X lying in a second plane spaced above the first plane, the protrusion extending up from said at least one lever arm and extending at least from said first plane to said second plane, said protrusion being operatively connected to the handle plunger.

7. A surgical instrument handle as set forth in claim 6 wherein said at least one lever arm comprises first and second lever arms connected to the handle body for lateral movement thereof relative to the handle axis between inward and outward positions and wherein said at least one protrusion constitutes first and second protrusions, the first protrusion extending up from the first lever arm, the second protrusion extending up from the second lever arm the first and second protrusions being operatively connected to the handle plunger for moving the handle plunger between its forward and rearward positions as said lever arms are moved between their inward and outward positions.

8. A surgical instrument handle as set forth in claim 7 further comprising a pair of links, each link having a first end connected to one of the protrusions and a second end connected to the handle plunger.

9. A surgical instrument handle as set forth in claim 6 wherein the handle body comprises a handle stationary part and a handle rotor rotatably connected to the handle stationary part for rotation about the instrument axis X, the handle rotor being configured for fixedly receiving the head static part so that rotation of the handle rotor relative to the handle stationary part causes like rotation of the surgical instrument head when the head static part is attached to the handle rotor.

10. A surgical instrument comprising:

a surgical instrument head having a proximal end, a distal end forward of the proximal end and insertable into a patient, a head static part at the proximal end, a reciprocative part generally at the proximal end, and a moveable distal part at the distal end, the moveable distal part being moveable relative to the head static part between a first position and a second position for enabling a surgeon to perform a surgical procedure on the patient, the reciprocative part being reciprocally moveable relative to the head static part generally along an instrument axis X between a forward position and a rearward position, said reciprocative part being operatively connected to said moveable distal part so that movement of the reciprocative part between its forward and rearward positions causes movement of the moveable distal part between its first and second positions; and a surgical instrument handle having a handle body attachable to the head static part of the surgical instrument head, a handle plunger configured for reciprocating motion relative to the handle body generally along the instrument axis X between forward and rearward positions, and at least one lever arm;

the handle body comprising a handle stationary part and a handle rotor rotatably connected to the handle stationary part for rotation about the instrument axis X, the handle rotor being configured for fixedly receiving the head static part so that rotation of the handle rotor relative to the handle stationary part causes like rotation of the surgical instrument head when the head static part is attached to the handle rotor;

the handle plunger being operatively engageable with the reciprocative part of the surgical instrument head when the head static part is attached to the handle body, the handle plunger being configured so that movement of the handle plunger between its forward and rearward positions causes movement of the reciprocative part of the surgical instrument head between its forward and rearward positions;

said at least one lever arm being connected to the handle body for lateral movement thereof relative to the handle axis between inward and outward positions, said at least one lever arm being configured for being engaged and laterally reciprocated between its inward and outward positions by a hand of a surgeon, said at least one lever arm being operatively connected to the handle plunger for moving the handle plunger between its forward and rearward positions as said at least one lever arm is moved between its inward and outward positions;

said surgical instrument handle being configured so that said lateral movement of said at least one lever arm is in a plane spaced below the handle plunger to provide a forward line of sight generally along the instrument axis X to the distal end of the surgical instrument head as viewed from behind the handle plunger for permitting the surgeon's hand to move said at least one lever arm between its inward and outward positions without blocking the line of sight.

11. A surgical instrument as set forth in claim 10 wherein said at least one lever arm comprises a pair of lever arms connected to the handle body for lateral movement thereof relative to the handle axis between inward and outward positions, said lever arms being operatively connected to the handle plunger for moving the handle plunger between its forward and rearward positions as said lever arms are moved between their inward and outward positions.

12. A surgical instrument as set forth in claim 11 further comprising a pair of protrusions, each protrusion extending up from one of the lever arms and being operatively connected to the handle plunger.

13. A surgical instrument as set forth in claim 12 further comprising a pair of links, each link having a first end connected to one of the protrusions and a second end connected to the handle plunger.

14. A surgical instrument as set forth in claim 13 wherein the handle body comprises a handle stationary part and a handle rotor rotatably connected to the handle stationary part for rotation about the instrument axis X, the handle rotor being configured for fixedly receiving the head static part so that rotation of the handle rotor relative to the handle stationary part causes like rotation of the surgical instrument head when the head static part is attached to the handle rotor.

15. A surgical instrument handle for use with an elongate surgical instrument head, the surgical instrument head having a proximal end, a distal end forward of the proximal end and insertable into a patient, a head static part at the proximal end attachable to the surgical instrument, a reciprocative part generally at the proximal end, and a moveable distal part at the distal end, the moveable distal part being moveable relative to the head static part between a first position and a second position for enabling a surgeon to perform a surgical procedure on the patient, the reciprocative part being reciprocally moveable relative to the head static part generally along an instrument axis X between a forward position and a rearward position, said reciprocative part being operatively connected to said moveable distal part so that movement of the reciprocative part between its forward and rearward positions causes movement of the moveable distal part between its first and second positions, the surgical instrument handle comprising:

a handle body attachable to the head static part of the surgical instrument head;

a handle plunger configured for reciprocating motion relative to the handle body generally along the instrument axis X between forward and rearward positions, the handle plunger being operatively engageable with the reciprocative part of the surgical instrument head when the head static part is attached to the handle body, the handle plunger being configured so that movement of the handle plunger between its forward and rearward positions causes movement of the reciprocative part of the surgical instrument head between its forward and rearward positions; and at least one lever arm connected to the handle body for lateral movement thereof relative to the handle axis between inward and outward positions, said at least one lever arm being configured for being engaged and laterally reciprocated between its inward and outward positions by a hand of a surgeon, said at least one lever arm being operatively connected to the handle plunger for moving the handle plunger between its forward and rearward positions as said at least one lever arm is moved between its inward and outward positions, the lever arm having a forward portion projecting forwardly beyond the head static part of the surgical instrument head when the head static part is attached to the handle body;

said surgical instrument handle being configured so that said lateral movement of said at least one lever arm is in a plane spaced below the handle plunger to provide a forward line of sight generally along the instrument axis X to the distal end of the surgical instrument head as viewed from behind the handle plunger for permitting the surgeon's hand to move said at least one lever arm between its inward and outward positions without blocking the line of sight.

16. A surgical instrument handle as set forth in claim 15 wherein the handle body comprises a handle stationary part and a handle rotor rotatably connected to the handle stationary part for rotation about the instrument axis X, the handle rotor being configured for fixedly receiving the head static part so that rotation of the handle rotor relative to the handle stationary part causes like rotation of the surgical instrument head when the head static part is attached to the handle rotor.

17. A surgical instrument handle as set forth in claim 16 further comprising a handle bare in the handle stationary part for receiving the handle plunger, said handle bore and said handle plunger being configured so that movement of said at least one lever arm between its inward and outward positions causes the handle plunger to move in the handle bore between its forward and rearward positions.

18. A surgical instrument handle as set forth in claim 15 further comprising at least one protrusion extending up from said at least one lever arm and being operatively connected to the handle plunger.

19. A surgical instrument handle as set forth in claim 18 wherein said at least one lever arm comprises first and second lever arms connected to the handle body for lateral movement thereof relative to the handle axis between inward and outward positions and wherein said at least one protrusion constitutes first and second protrusions, the first protrusion extending up from the first lever arm, the second protrusion extending up from the second lever arm, the first and second protrusions being operatively connected to the handle plunger for moving the handle plunger between its forward and rearward positions as said lever arms are moved between their inward and outward positions.

20. A surgical instrument handle as set forth in claim 15 wherein the forward portion of the lever arm projects forwardly beyond the handle body.

* * * * *